United States Patent
Kwon et al.

(10) Patent No.: US 11,096,979 B2
(45) Date of Patent: Aug. 24, 2021

(54) PHARMACEUTICAL COMPOSITION FOR PREVENTING OR TREATING LIVER DISEASES, CONTAINING LICORICE EXTRACT CONTAINING GLYCYRRHIZIN AND LIQUIRITIN

(71) Applicant: NOVAREX CO., LTD., Cheongju-si (KR)

(72) Inventors: Suk-Hyung Kwon, Seoul (KR); Jae-Chul Jung, Cheonan-si (KR); Kyung-Mi Kim, Cheongju-si (KR)

(73) Assignee: NOVAREX CO., LTD., Cheongju-si (KR)

( * ) Notice: Subject to any disclaimer, the term of this patent is extended or adjusted under 35 U.S.C. 154(b) by 0 days.

(21) Appl. No.: 16/096,124

(22) PCT Filed: May 26, 2016

(86) PCT No.: PCT/KR2016/005593
§ 371 (c)(1),
(2) Date: Oct. 24, 2018

(87) PCT Pub. No.: WO2017/188499
PCT Pub. Date: Nov. 2, 2017

(65) Prior Publication Data
US 2019/0134130 A1    May 9, 2019

(30) Foreign Application Priority Data

Apr. 25, 2016  (KR) .......................... 10-2016-0050155

(51) Int. Cl.
| | |
|---|---|
| *A61K 36/484* | (2006.01) |
| *A61K 31/704* | (2006.01) |
| *A61K 31/352* | (2006.01) |
| *A61K 9/00* | (2006.01) |
| *A61K 9/16* | (2006.01) |
| *A23L 33/105* | (2016.01) |
| *A61P 1/16* | (2006.01) |
| *A61K 31/7034* | (2006.01) |
| *A61K 47/36* | (2006.01) |
| *B01D 11/02* | (2006.01) |

(52) U.S. Cl.
CPC .......... *A61K 36/484* (2013.01); *A23L 33/105* (2016.08); *A61K 9/0053* (2013.01); *A61K 9/1652* (2013.01); *A61K 9/1682* (2013.01); *A61K 31/352* (2013.01); *A61K 31/704* (2013.01); *A61K 31/7034* (2013.01); *A61K 47/36* (2013.01); *A61P 1/16* (2018.01); *B01D 11/0288* (2013.01); *A23V 2002/00* (2013.01); *A61K 2236/00* (2013.01)

(58) Field of Classification Search
CPC .... A61K 31/352; A61K 9/1652; A61K 47/36; A61K 9/0053; A61K 31/704; A61K 36/484; A61K 31/7034; A61K 9/1682; A61K 2236/00; A61K 2300/00; B01D 11/0288; A23L 33/105; A61P 1/16; A61V 2002/00; A61V 2250/334; A61V 2250/21; A61V 2250/2116; A61V 2250/252; A23V 2250/5114

See application file for complete search history.

(56) References Cited

FOREIGN PATENT DOCUMENTS

| KR | 10-0697056 B1 | 3/2007 |
|---|---|---|
| KR | 10-1581240 B1 | 12/2015 |

OTHER PUBLICATIONS (R) Ji et al., "Bioactive Constituents of *Glycyrrhiza uralensis* (Licorice); Discovery of the Effective Components of a Traditional Herbal Medicine," Journal of Natural Products, 79(2), 281-292 (Feb. 3, 2016).*
(S) Chen et al., "Glycyrrhetinic Acid Supporesses NF-kappaB Activation in TNF-alpha Induced Heptatocytes," Journal of Agricultural and Food Chemistry, 62(3), 618-625 (Jan. 5, 2014).*
Lee et al., "Protective Mechanism of Glycyrrhizin on Acute Liver Injury Induced by Carbon Tetrachloride in Mice", Biol. Pharm. Bull., vol. 30, No. 10, pp. 1898-1904, (2007).

* cited by examiner

*Primary Examiner* — Lawrence E Crane
(74) *Attorney, Agent, or Firm* — Vorys, Sater, Seymour & Pease LLP; Mih Suhn Koh

(57) ABSTRACT

Disclosed is a composition containing a licorice extract comprising glycyrrhizin and liquiritin at a content ratio of 1.5 to 1.8:1, obtained by performing extraction on licorice, adding an excipient and performing spray drying. The composition containing the licorice extract can be efficiently used as a pharmaceutical composition for the prevention or treatment of liver disease or a food composition for the improvement of liver function in the pharmaceutical and food industry fields.

1 Claim, 17 Drawing Sheets

[Figures]
[Figure 1 A]
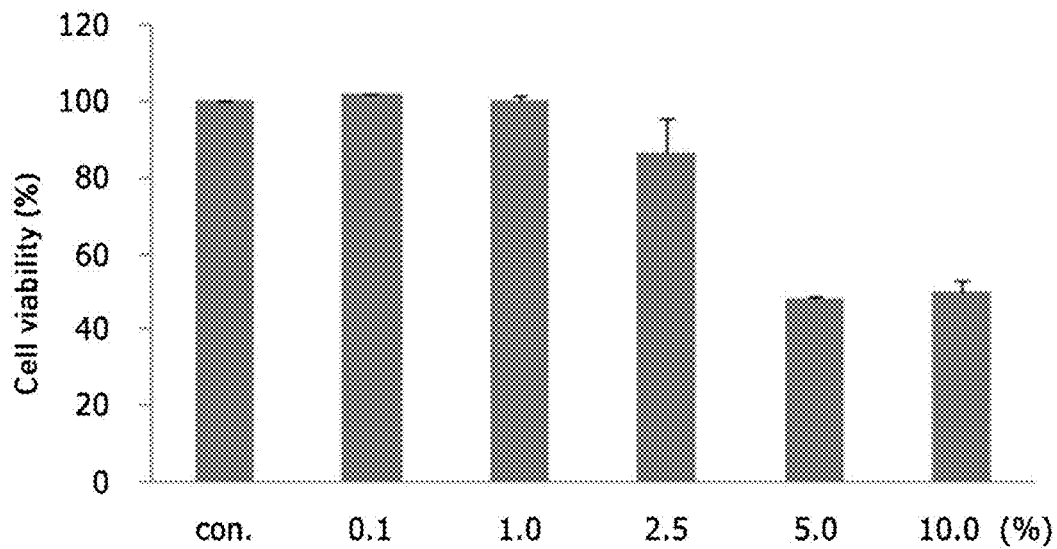
[Figure 1 B]
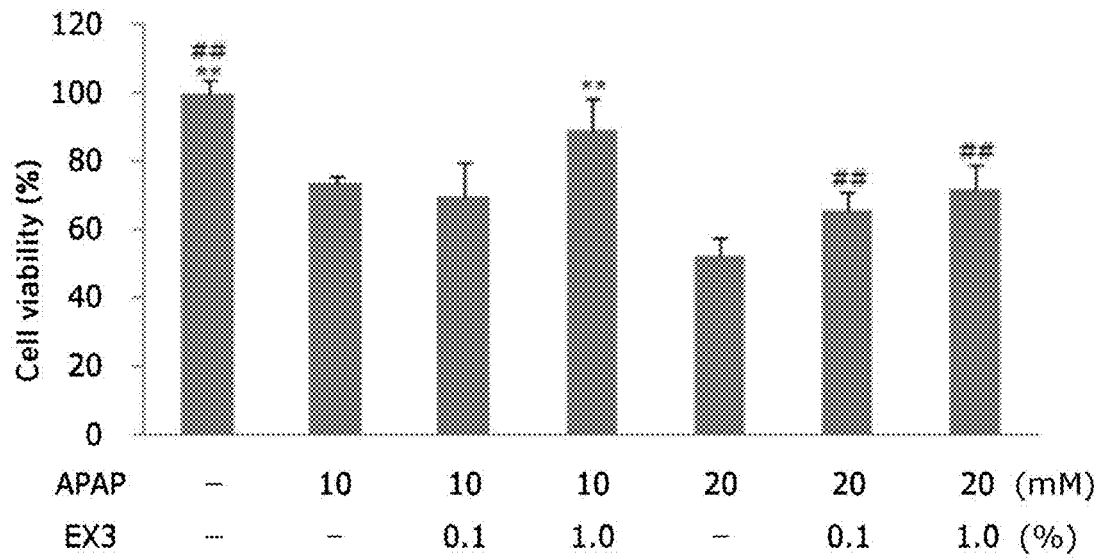

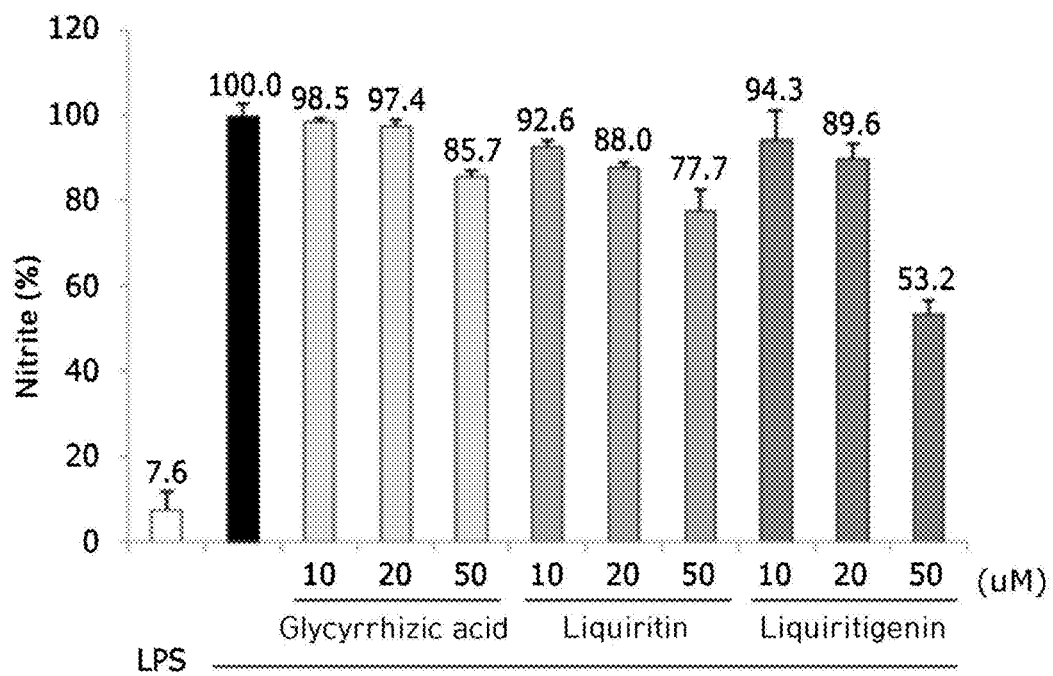
[Figure 2]

[Figure 3A]
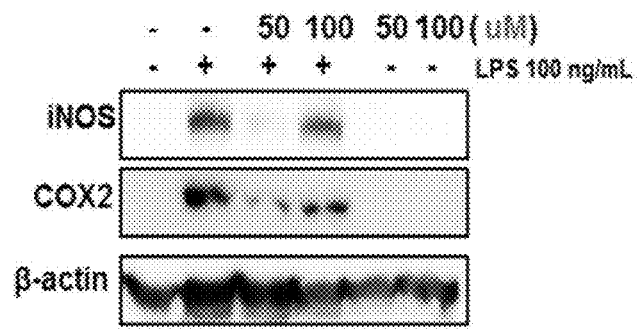
[Figure 3B]
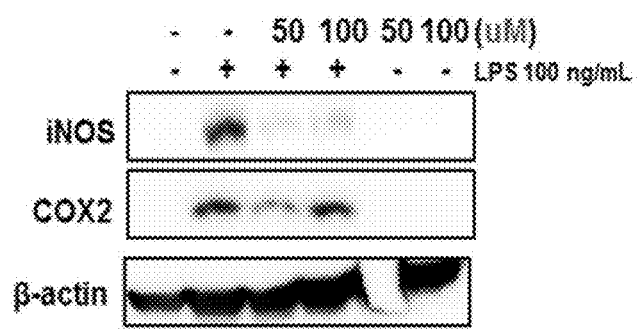
[Figure 3C]
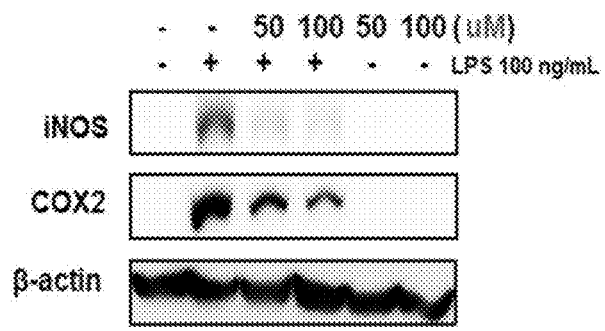

[Figure 4A]
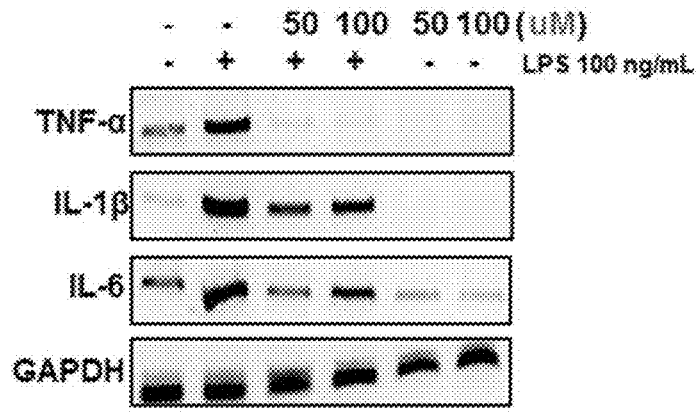
[Figure 4B]
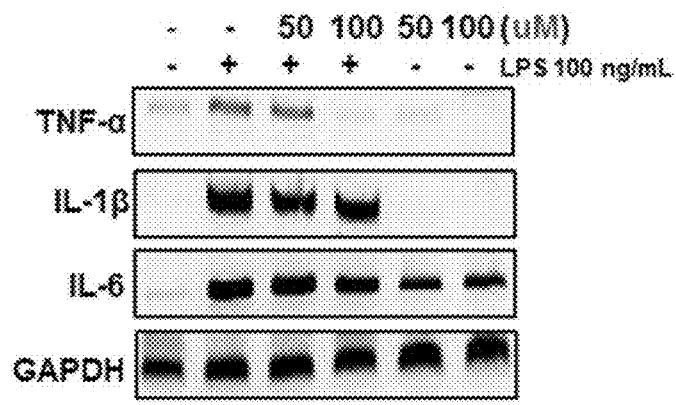
[Figure 4C]
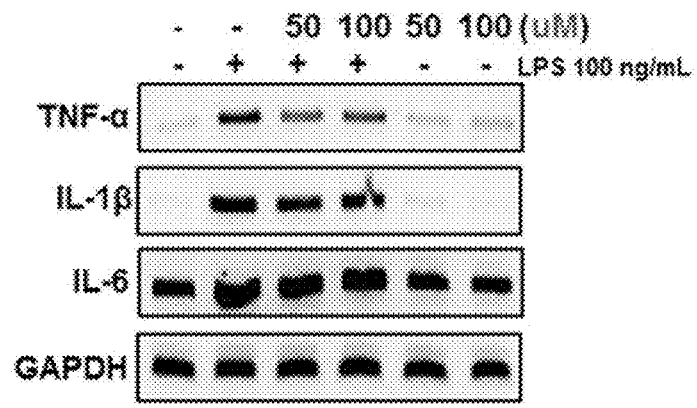

[Figure 5A]
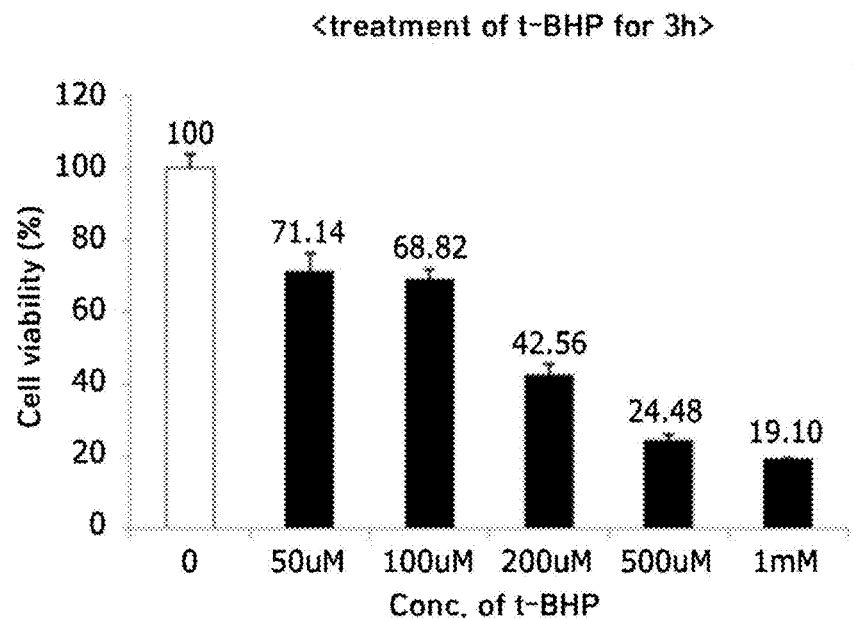
[Figure 5B]
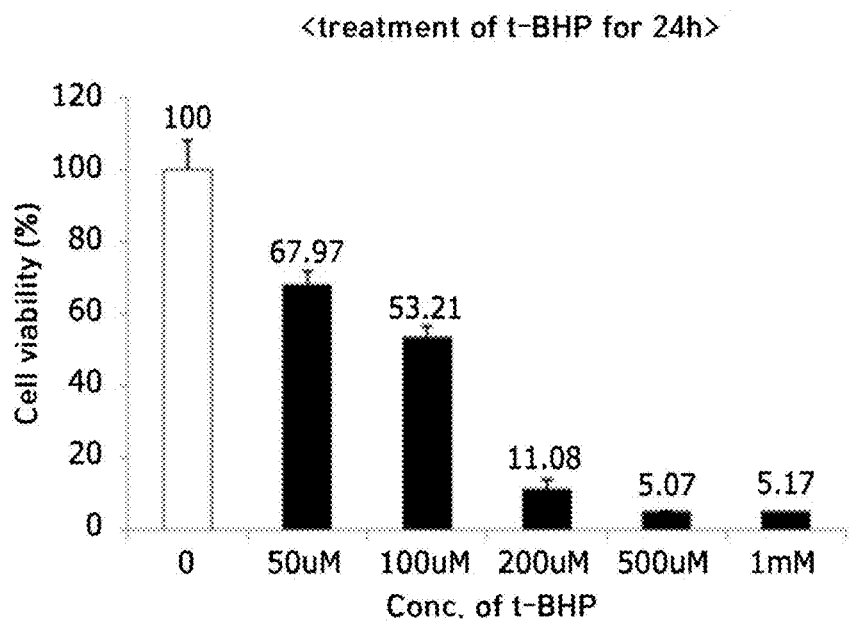

[Figure 6]
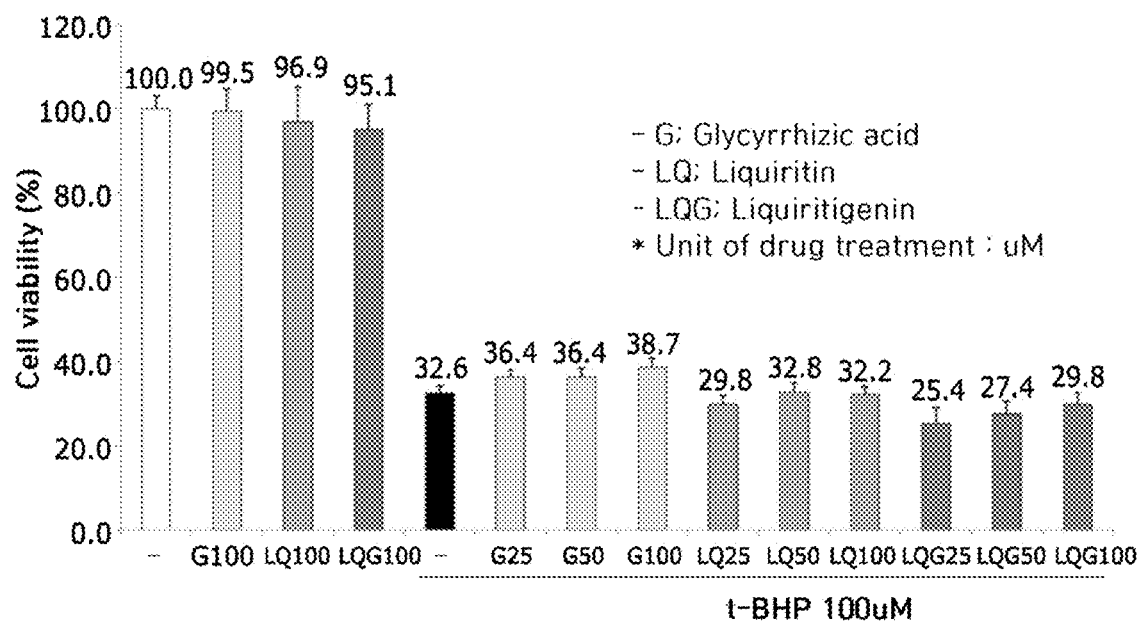

[Figure 7A]
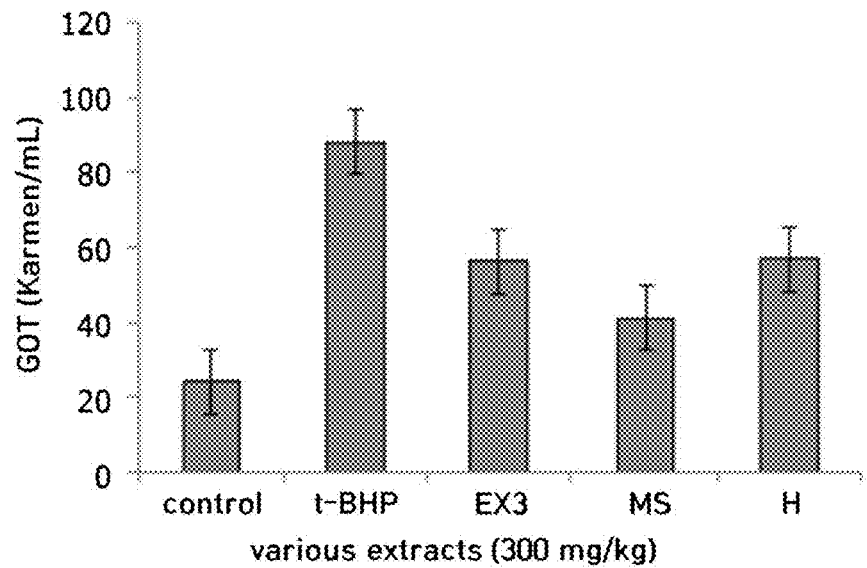
[Figure 7B]
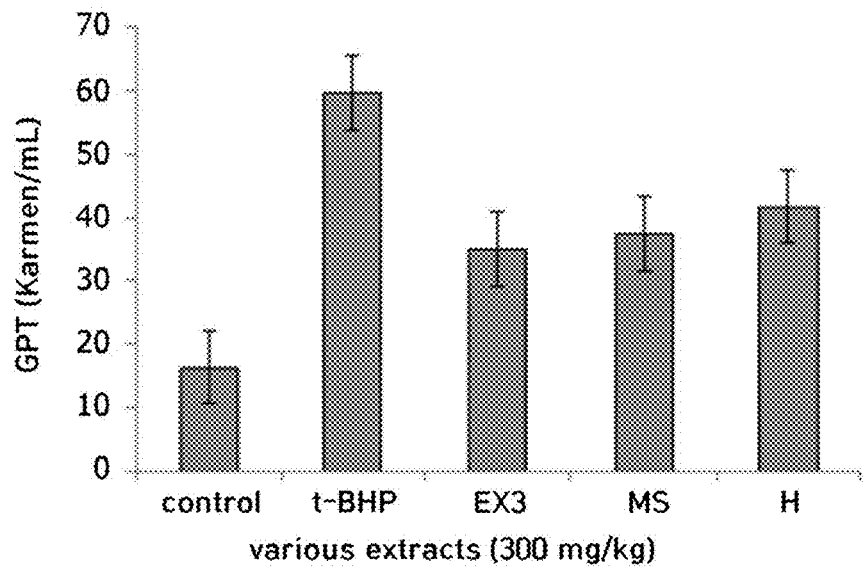

[Figure 8A]
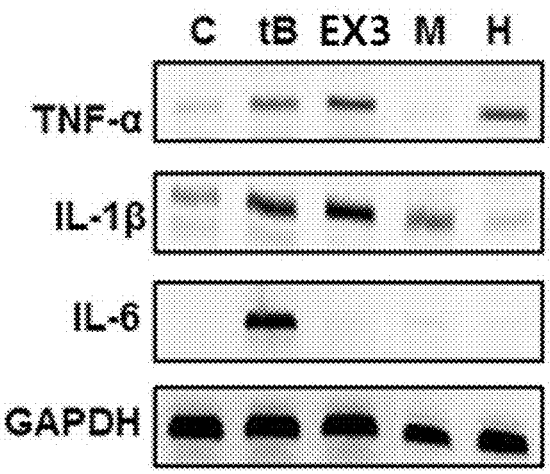
tBHP - 1.5 mmol/kg
i.p. injection
[Figure 8B]
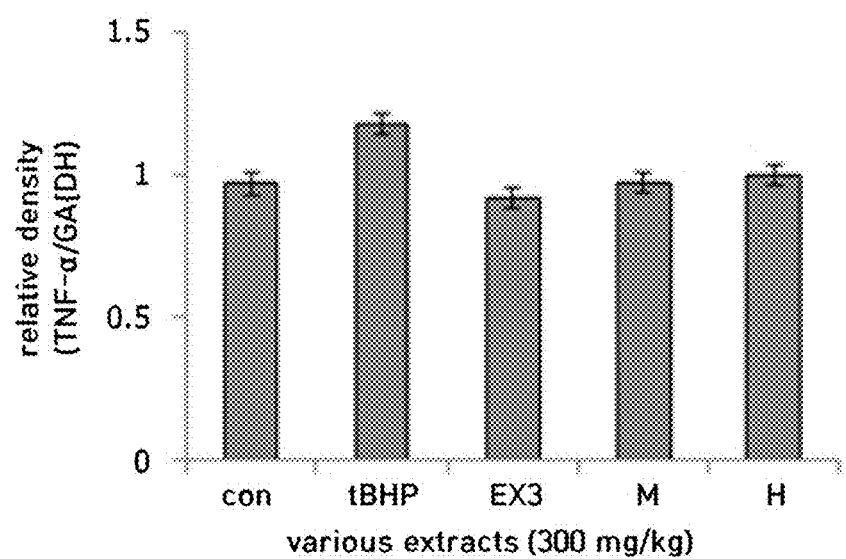

[Figure 8C]
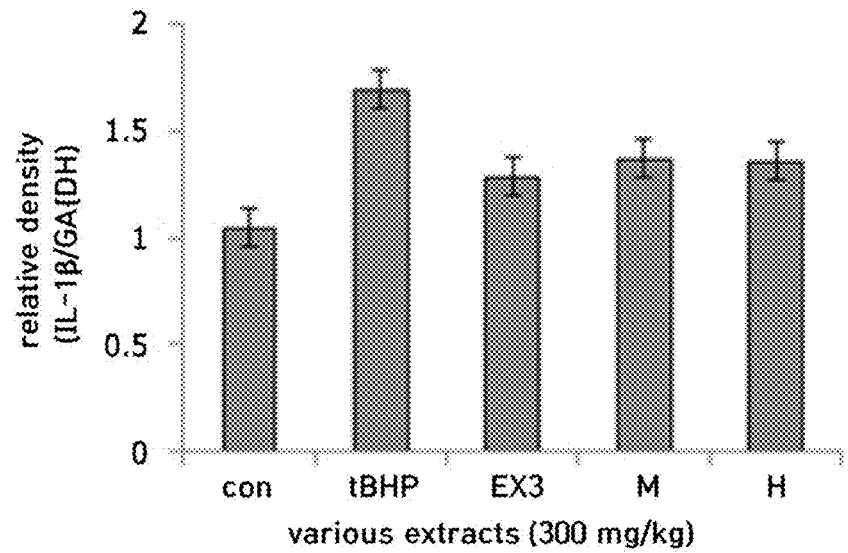
[Figure 8D]
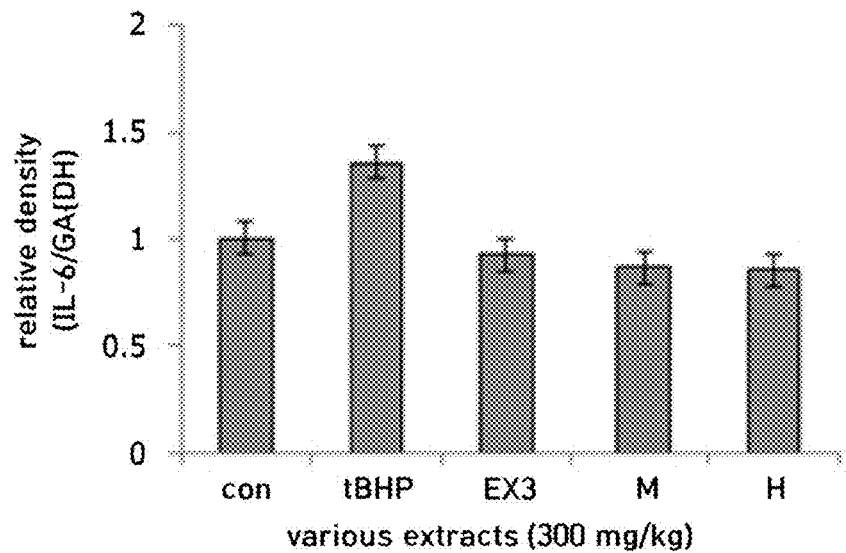

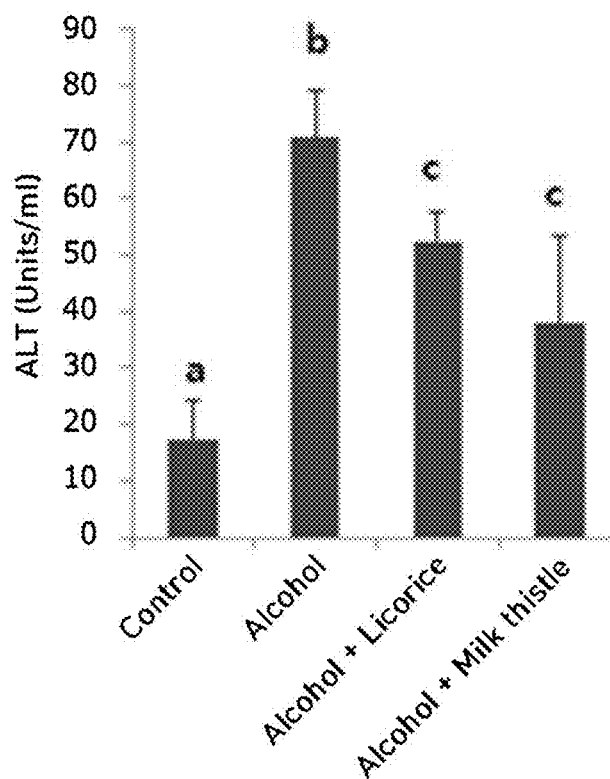
[Figure 9A]

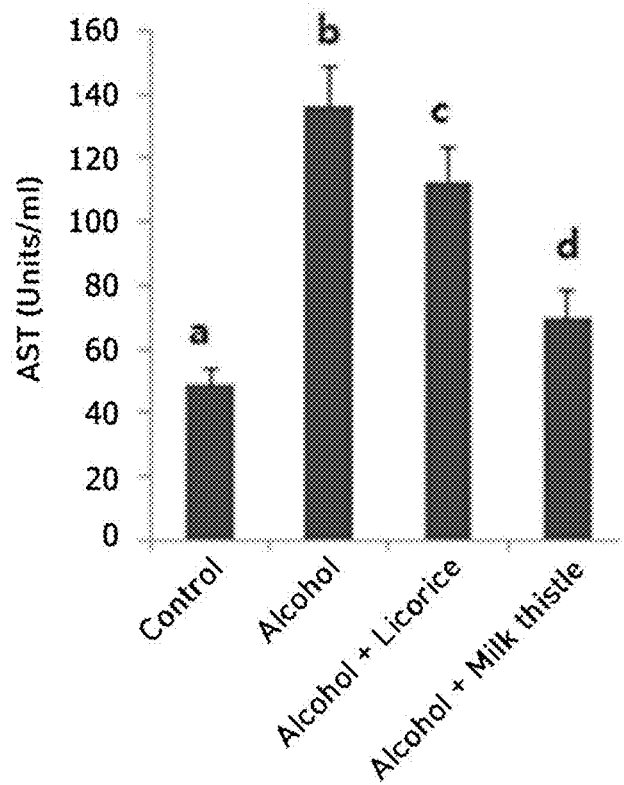
[Figure 9B]

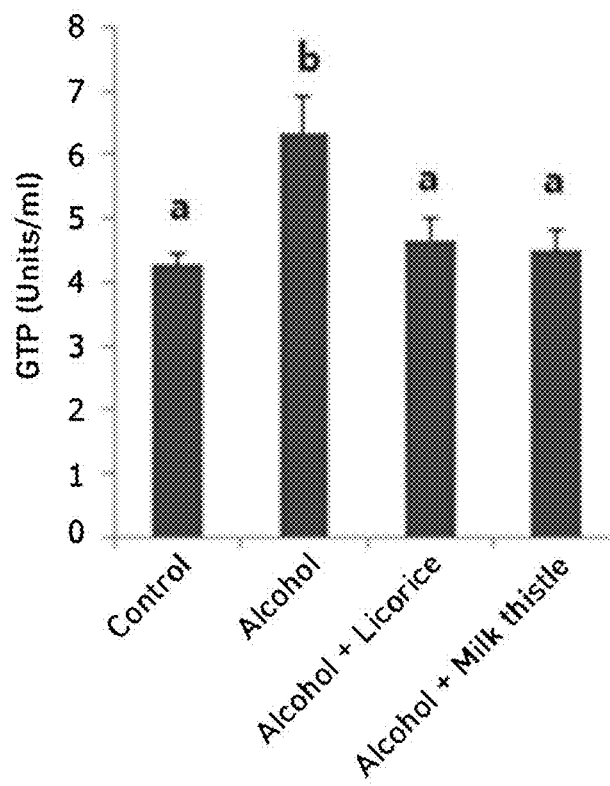
[Figure 9C]

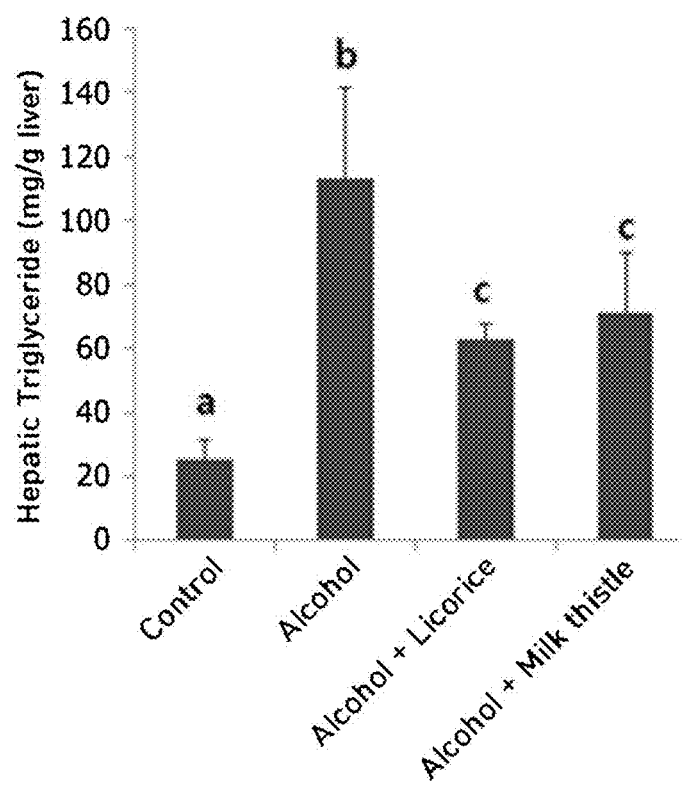
[Figure 10A]

[Figure 10B]
a. Control
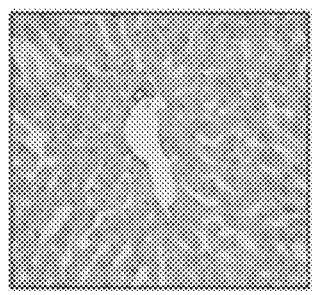
b. Alcohol
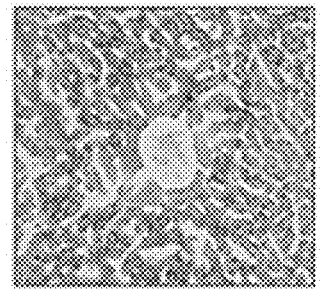
c. Alcohol + Licorice
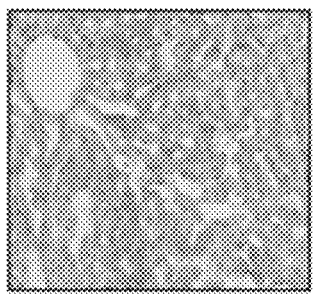
d. Alcohol + Milk thistle
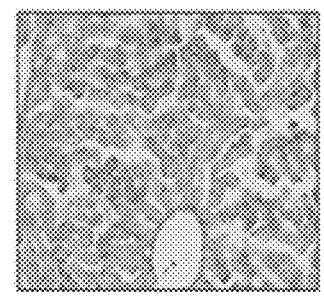

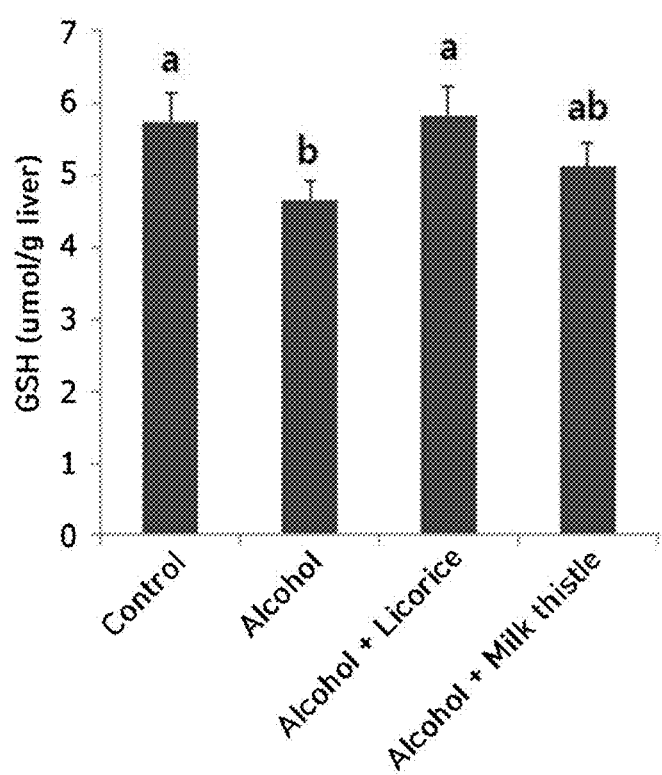
[Figure 11]

[Figure 12A]
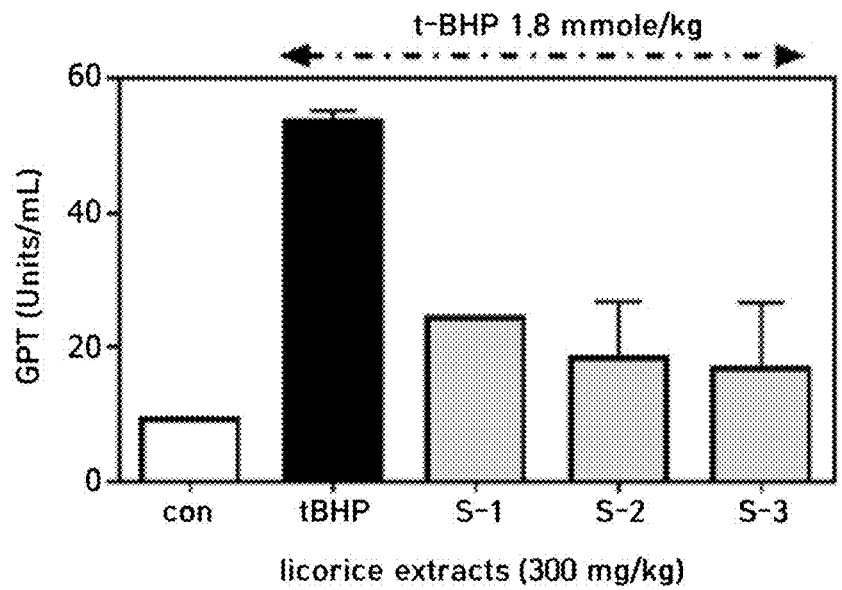
[Figure 12B]
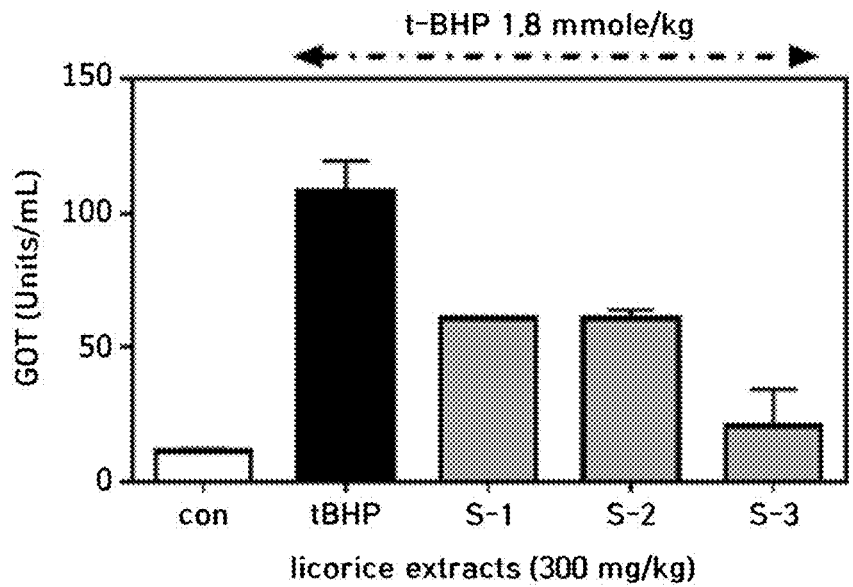

[Figure 13]
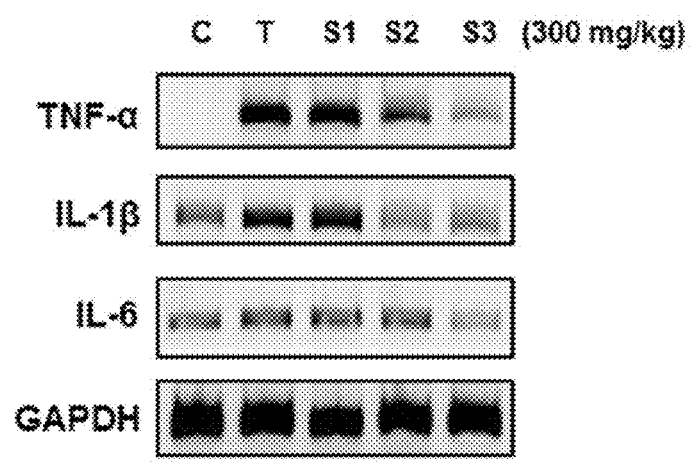

PHARMACEUTICAL COMPOSITION FOR PREVENTING OR TREATING LIVER DISEASES, CONTAINING LICORICE EXTRACT CONTAINING GLYCYRRHIZIN AND LIQUIRITIN

CROSS-REFERENCE TO RELATED APPLICATIONS

This application claims priority to and the benefit of Korean Patent Application No. 10-2016-0050155 filed on Apr. 25, 2016 and International Patent Application No. PCT/KR2016/005593, filed on May 26, 2016, the disclosure of which is incorporated herein by reference in its entirety.

TECHNICAL FIELD

The present invention relates to a pharmaceutical composition for the prevention or treatment of liver disease containing a licorice extract, and more particularly to a pharmaceutical composition for the prevention or treatment of liver disease containing a licorice extract comprising glycyrrhizin and liquiritin at a predetermined ratio.

BACKGROUND ART

Licorice (Glycyrrhizae Radix et Rhizoma) is a perennial herb belonging to the family Leguminosae, and the root or rootstock of Glycyrrhiza uralensis Fischer, G. glabra Linne, and G. inflata Batal is used as it is or after removing the shell therefrom. Licorice grows wild in arid desert climates in China's Inner Mongolia or northeast Heilongjiang, Siberia, Spain or southern Italy, and Iran and Iraq of the Middle East, and in Korea licorice cultivation is known to be appropriate only in the climatic conditions in the Hamkyung Province and North Chungcheong Province mountains (the section "Licorice", DonguiBogam). In particular, Jecheon licorice, cultivated in Korea, is produced under the Good Agricultural Practice (GAP) guidelines, which manages hazardous factors from the production stage to the distribution and sales stage so that consumers can receive safe and hygienic supplies.

Licorice is reported to contain a flavonoid-based physiologically active material such as glycyrrhetic acid, liquiritin apioside, isoliquiritin and glabridin, etc.; an isoflavonoid-based material such as licoricidin and glabra, etc.; a coumarin derivative component such as herniarin, umbelliferone, etc.; and an amino acid component such as alanine, asparagine, glycine, etc.

Also, licorice is reported to include the components of Chemical Formulas 1 to 4 below.

<Chemical Formula 1>

1: Glycyrrhizic acid $R_1$ = gluA, $R_2$ = h
2: Uralsaponin B, $R_1$ = H, $R_2$ = gluA <Chemical Formula 2>

3: Liquiritin, $R_1$ = glucoside, $R_2$ = H
4: Liquiritin, apioside, $R_1$ = glu-epi, $R_2$ = H
5: Neoliquiritin, $R_1$ = H, $R_2$ = glucoside
6: Liquiritigenin, $R_1$ = $R_2$ = H <Chemical Formula 3>

7: Licoarylcoumarin

<Chemical Formula 4>

8: Licorice glycoside A

Meanwhile, interest in alcoholic liver disease has been increasing with an increase in alcohol consumption worldwide every year. Particularly in Korea, as the frequency of alcohol consumption per person increases, interest in hepatoprotective efficacy increases, and further study on the hepatoprotective effects of plant extracts is needed. Generally, some herbal medicines for liver disease are very popular, but have not been accepted as methods of treating liver disease. The reasons for this are (i) lack of standardization of herbal medicine and confirmation of active components, (ii) lack of randomized controlled trials (RCTs), and (iii) lack of toxicity assessment (Dhiman and Chawla, Digestive Diseases and Sciences, 50(10): 1807-1812, 2005).

Research into the efficacies and major components of plant extracts exhibiting hepatoprotective effects has not been sufficiently carried out to date. Therefore, the development of a plant extract that has no toxicity and exhibits a hepatoprotective effect related to components therein is required.

DISCLOSURE

Technical Problem

The present inventors have studied plant extracts having hepatoprotective effects and have ascertained that a licorice extract comprising glycyrrhizin and liquiritin at a content ratio of 1.5 to 1.8:1, obtained by performing extraction on licorice, adding an excipient and performing spray drying, is non-toxic and exhibits hepatoprotective efficacy upon testing in vitro and in vivo, whereby the licorice extract prepared through the above extraction process may be used as a pharmaceutical composition for the prevention or treatment of liver disease.

Accordingly, the present invention is intended to provide a pharmaceutical composition for the prevention or treatment of liver disease containing a licorice extract comprising glycyrrhizin and liquiritin at a content ratio of 1.5 to 1.8:1, obtained by extraction, addition with an excipient and spray drying.

Technical Solution

An aspect of the present invention provides a pharmaceutical composition for preventing or treating a liver disease containing a licorice extract, the licorice extract being prepared by a preparation method comprising: (a) performing extraction on licorice twigs with 50 to 80% ethanol for 1 to 5 hr; (b) concentrating the extract; and (c) adding the concentrated extract with an excipient and performing spray drying, and the licorice extract comprising glycyrrhizin and liquiritin at a content ratio of 1.5 to 1.8:1.

In an embodiment, the excipient in step (c) may be dextrin. Also, in step (c), the spray drying may be performed at a concentrated extract temperature of 70 to 90° C. and a blowing temperature of 150 to 190° C.

In an embodiment, the liver disease may be hepatitis or fatty liver disease, and is preferably alcoholic fatty liver disease.

In an embodiment, the pharmaceutical composition may further contain a pharmaceutically acceptable diluent or carrier.

Another aspect of the present invention provides a food composition for improving a liver function containing a licorice extract, the licorice extract being prepared by a preparation method comprising: (a) performing extraction on licorice twigs with 50 to 80% ethanol for 1 to 5 hr; (b) concentrating the extract; and (c) adding the concentrated extract with an excipient and performing spray drying, and the licorice extract comprising glycyrrhizin and liquiritin at a content ratio of 1.5 to 1.8:1.

In an embodiment, the excipient in step (c) may be dextrin. Also, in step (c), the spray drying may be performed at a concentrated extract temperature of 70 to 90° C. and a blowing temperature of 150 to 190° C.

In an embodiment, the food composition may be provided in the form of a functional food, a nutritional supplement, a health food or a food additive.

Advantageous Effects

According to the present invention, the licorice extract has no toxicity to hepatocytes, exhibits GOT/GPT reduction efficacy similar or superior to that of a positive control group (milk thistle extract) having hepatoprotective efficacy, and inhibits an increase in expression of proinflammatory cytokines such as TNF-α, IL-1β, and IL-6 in liver tissue and can thus exhibit hepatoprotective effect. In particular, the licorice extract is found to protect liver function in that it significantly lowered the levels of ALT, AST and GPT, which increase as a result of liver injury in an alcoholic liver injury model, remarkably reduced fat accumulation due to alcohol, and exhibited superior maintenance effect of an endogenous antioxidant.

Therefore, the licorice extract of the present invention can be efficiently used as a pharmaceutical composition for the prevention or treatment of liver disease or a food composition for the improvement of liver function in the pharmaceutical and food industry fields.

DESCRIPTION OF DRAWINGS

FIG. 1A shows the results of treatment of cultured hepatocytes (HepG2) with a licorice extract; FIG. 1B shows a graph of cell viability after treatment of cultured hepatocytes (HepG2), having hepatotoxicity induced by acetaminophen, with a licorice extract (APAP: acetaminophen, Licorice A: Licorice extract 3);

FIG. 2 is a graph showing the results of evaluation of the effects of three components (glycyrrhizin, liquiritin and liquiritigenin) contained in the licorice extract on inhibiting NO production by LPS in BV2 cells;

FIGS. 3A, 3B and 3C shows the results of measurement of inflammatory molecular biological indicators (iNOS, COX2) of three components [(3A) glycyrrhizin, (3B) liquiritin, (3C) liquiritigenin] contained in the licorice extract;

FIGS. 4A, 4B and 4C shows the results of measurement of inflammatory molecular biological indicators (TNF-α, IL-1β, IL-6) of three components [ (4A) glycyrrhizin, (4B) liquiritin, (4C) liquiritigenin] contained in the licorice extract;

FIGS. 5A and 5B is graphs showing the extent of hepatotoxicity induced by t-BHP depending on the dose and treatment time in HepG2 cells;

FIG. 6 is a graph showing the effects of active components in licorice on inhibiting hepatotoxicity induced by t-BHP (G: glycyrrhizin, LQ: liquiritin, LQG: liquiritigenin);

FIGS. 7A and 7B is graphs showing the hepatoprotective effect in mice through treatment with the licorice extract (control: control group, EX3: Licorice extract 3, M: milk thistle extract);

FIGS. 8A, 8B, 8C and 8D shows the results of western blotting and the graphs thereof showing the expression of proinflammatory cytokines through treatment with the licorice extract in liver tissue having hepatotoxicity induced by t-BHP;

FIGS. 9A, 9B and 9C is graphs showing changes in (9A) ALT, (9B) AST, and (9C) GTP in the blood due to chronic alcohol supply (ANOVA followed by a Newman-Keuls multiple range test, P<0.05);

FIG. 10A is a graph showing changes in fat content in the liver due to chronic alcohol supply and FIG. 10B is images showing fat accumulation (ANOVA followed by a Newman-Keuls multiple range test, P<0.05);

FIG. 11 is a graph showing changes in GSH of liver due to chronic alcohol supply (ANOVA followed by a Newman-Keuls multiple range test, P<0.05);

FIGS. 12A and 12B is graphs showing the hepatoprotective effects of the licorice extracts depending on the type of extraction process (S-1: Licorice extract 1, S-2: Licorice extract 2, S-3: Licorice extract 3); and FIG. 13 shows the results of measurement of molecular biomarkers (TNF-α, IL-1β, IL-6) related to anti-inflammatory efficacy after treatment of mice with the licorice extract depending on the type of extraction process.

BEST MODE

The present invention pertains to a pharmaceutical composition for preventing or treating of a liver disease containing a licorice extract, the licorice extract being prepared by a preparation method comprising: (a) performing extraction on licorice twigs with 50 to 80% ethanol for 1 to 5 hr; (b) concentrating the extract; and (c) adding the concentrated extract with an excipient and performing spray drying, the licorice extract comprising glycyrrhizin and liquiritin at a content ratio of 1.5 to 1.8:1.

The process of performing extraction on licorice is conducted such that the content ratio of glycyrrhizin and liquiritin is adjusted to 1.5 to 1.8:1 by decreasing the amount of glycyrrhizin, which is a saponin-based compound having adverse effects, and increasing the amount of liquiritin, which is a type of flavonoid.

Step (a) is performing extraction on licorice twigs with 50 to 80% ethanol for 1 to 5 hr.

In the present invention, the extraction process may be performed through any extraction process for preparing a licorice extract as known in the art, and is preferably conducted at 15 to 40° C. The extraction time may fall in the range of 1 to 5 hr, and preferably 2 to 4 hr. The extraction solvent may be 50 to 80% ethanol, and preferably 70% ethanol.

As pretreatment procedures of licorice before extraction, sorting, water washing and cutting may typically be performed, and filtration may be carried out after extraction.

Step (b) is concentrating the extract.

The concentration process is removing the solvent from the solution to increase the concentration of a solute. The extract may be concentrated using a concentration device or a concentration process known in the art, for example, precipitation, evaporation, vacuum evaporation, ultrafiltration, reverse osmosis, and centrifugation.

In the present invention, the concentration process is preferably implemented through vacuum evaporation at 35 to 50° C.

Step (c) is adding the concentrated extract with an excipient and performing spray drying.

The drying may be performed through spray drying or freeze drying, and preferably the spray drying is conducted under conditions of a concentrated solution temperature of 70 to 90° C. and a blowing temperature of 150 to 190° C., and more preferably a concentrated solution temperature of 75 to 80° C. and a blowing temperature of 170 to 180° C.

The excipient may include dextrin, lactose, starch, and cellulose, and preferably dextrin is used. Dextrin is preferably added in an amount of 10 to 20 wt % based on the amount of the concentrated licorice solution.

In an embodiment, the liver disease may be hepatitis or fatty liver disease, and is preferably alcoholic fatty liver disease.

In an embodiment, the pharmaceutical composition may further contain a pharmaceutically acceptable diluent or carrier. Specifically, the pharmaceutical composition of the present invention may contain a pharmaceutically acceptable carrier, and may be formulated as oral dosage forms, such as powder, granule, tablet, capsule, suspension, emulsion, syrup, and aerosol formulations, as well as formulations for external use, suppositories and sterile injectable solutions, in accordance with typical individual processes. The pharmaceutically acceptable carrier may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil, and may also include excipients or diluents such as fillers, extenders, binders, wetting agents, disintegrants, surfactants, and the like. An oral solid formulation may include tablets, pills, powders, granules, capsules, and the like, and such a solid formulation may include at least one excipient, for example, starch, calcium carbonate, sucrose, lactose, gelatin, and the like, and may also include lubricants such as magnesium stearate, talc, etc. An oral liquid formulation may include suspensions, solutions, emulsions, syrups and the like, and may also include diluents, such as water or liquid paraffin, wetting agents, sweeteners, fragrances, and preservatives. A parenteral formulation may include sterilized aqueous solutions, non-aqueous solvents, suspensions, emulsions, freeze-dried preparations and suppositories. As non-aqueous solvents or suspensions, propylene glycol, polyethylene glycol, vegetable oil such as olive oil, injectable esters such as ethyl oleate, and the like may be used. As the base of the suppositories, Witepsol, Macrogol, Tween 61, cacao butter, laurin fat, glycerogelatin and the like may be used.

The amount of the licorice extract contained in the pharmaceutical composition of the present invention, when administered, may vary depending on the conditions and body weights of patients, the severity of disease, the drug form, and the administration route and time, and may be appropriately selected by those skilled in the art. For example, the licorice extract may be administered in an amount of 0.0001 to 1000 mg/kg/day, and preferably 0.01 to 1000 mg/kg/day, and the administration may be carried out once a day or several times a day. Also, the pharmaceutical composition of the present invention may contain 0.001 to 90 wt % of the licorice extract based on the total weight of the composition.

The pharmaceutical composition of the present invention may be administered to mammals such as rats, mice, livestock, humans, and the like, through various routes, for example, oral, intraperitoneal, intrarectal, intravenous, intramuscular, subcutaneous, intrauterine epidural or intracerebroventricular injections.

In addition, the present invention pertains to a food composition for improving a liver function containing a licorice extract, the licorice extract being prepared by a preparation method comprising: (a) performing extraction on licorice twigs with 50 to 80% ethanol for 1 to 5 hr; (b) concentrating the extract; and (c) adding the concentrated extract with an excipient and performing spray drying, and the licorice extract comprising glycyrrhizin and liquiritin at a content ratio of 1.5 to 1.8:1.

In an embodiment, the excipient in step (c) may be dextrin. Also, in step (c), the spray drying may be performed at a concentrated extract temperature of 70 to 90° C. and a blowing temperature of 150 to 190° C.

In an embodiment, the food composition may be provided in the form of a functional food, a nutritional supplement, a health food, or a food additive, and may be prepared in various forms in accordance with typical methods known in the art.

For example, as the health food, the licorice extract prepared by the method of the present invention may be prepared in the form of a tea, juice, or other beverage, or may be ingested through granulation, encapsulation and powdering. Also, the licorice extract prepared by the method of the present invention may be provided in the form of a composition by being mixed with a substance or an active component known to have an effect of enhancing the immune function.

Furthermore, the functional food may be prepared by adding the licorice extract prepared by the method of the present invention to beverages (including alcoholic beverages), fruits and processed foods thereof (e.g. canned fruits, bottled fruits, jams, marmalade, etc.), fish, meat and processed foods (e.g. ham, sausages, corned beef, etc.), breads and noodles (e.g. udon, buckwheat noodles, ramen noodles, spaghetti, macaroni, etc.), fruit juices, various drinks, cookies, taffy, dairy products (e.g. butter, cheese, etc.), edible vegetable oil, margarine, vegetable protein, retort foods, frozen foods, various seasonings (e.g. soybean paste, soy sauce, sauce, etc.), and the like.

In the food composition of the present invention, the amount of the licorice extract prepared by the method of the present invention is not particularly limited, but is preferably 0.01 to 50 wt % based on the amount of the finally prepared food. In order for the licorice extract prepared by the method of the present invention to serve in the form of a food additive, it may be prepared in the form of a powder or a concentrated solution.

A better understanding of the present invention will be given through the following examples and test examples, which are merely set forth to illustrate the present invention but are not to be construed as limiting the scope of the present invention.

EXAMPLES

1. Materials and Method

Licorice materials (raw materials) were supplied from Korean Licorice Farming Association Corporation in Jecheon, North Chungcheong Province, Korea, and were prepared using the following three methods.

(1) Licorice Extract 1 (EX1)

A licorice raw material (twigs, 30 g) was extracted at 50° C. for 3 hr using distilled water (270 g) and filtered with 40 mesh to remove residue, after which the extracted solution was concentrated through vacuum evaporation (40° C.) to remove the solvent, thereby preparing a sample. Extract 1 thus obtained was an oil-phase paste.

(2) Licorice Extract 2 (EX2)

A licorice raw material (twigs, 30 g) was extracted at 50° C. for 3 hr using 70% ethanol (270 g) and filtered with 40 mesh to remove residue, after which the extracted solution was concentrated through vacuum evaporation (40° C.) to completely remove the solvent, thereby preparing a sample. Extract 2 thus obtained was an oil-phase paste.

(3) Licorice Extract 3 (EX3)

A licorice raw material (twigs, 1 kg) was subjected to cyclic extraction for 3 hr using 70% ethanol (10 kg), and the extract was cooled to 30 to 35° C., after which filtration using a 75 μm cartridge and then centrifugation (15,000 rpm) were performed to remove licorice extraction residue, thus obtaining 0.9 kg of an extracted solution. The extracted solution was subjected to vacuum evaporation (55 to 58° C.) to remove residual ethanol and then concentrated to 20 brix, thus obtaining 0.3 kg of a concentrated solution. The concentrated solution was mixed with 0.3 kg of dextrin to dissolve, sterilized at 95° C. for 30 min, and spray dried (solution temperature of 75 to 80° C., blowing temperature of 180° C., atomizer of 18,000 rpm), thus preparing 0.23 kg of a licorice extract powder.

2. Analysis of Licorice Extract

In order to quantitatively/qualitatively analyze triterpenoid saponin-based glycyrrhizic acid (GA; glycyrrhizin) and flavonoid-based liquiritin (LQ) as active marker components of the licorice extract, content analysis was performed in accordance with the United States Pharmacopoeia (USP35, p. 1362-1364), the Korean Pharmacopoeia ($9^{th}$ revision, p. 903-905), the Codex Alimentarius Commission (CAC) regulations, AOAC methods, and the like.

(1) LC-MS/MS Conditions

In order to quantitatively analyze glycyrrhizin, liquiritin and liquiritigenin as main components of the licorice extract, digoxin was used as an internal standard material, and a column (LUNA C18 column, 2.0×150 mm, 5 μm) was used for separating individual material components. Using an HPLC (available from Shiseido) and ESI source (available from ABSIEX) mass spectrometer, analysis was performed (multiple reaction monitoring (MRM) mode) under the conditions shown in the following Table 1 [LC-MS/MS analysis conditions of licorice extract] and Table 2 [Mass measurement parameter of licorice functional component standard material].

(2) Obtaining of Calibration Curve

The calibration curves for glycyrrhizin, liquiritin and liquiritigenin relative to the standard were obtained by plotting concentrations of 12.5, 25, 50, 100, 300, 500, 1000, 2500 and 5000 ng/mL, and digoxin, as the internal standard material, was added at 500 ng/mL, and the calibration curves were obtained using the ratio of analyte to internal standard material. The linearity of the obtained calibration curve was determined by calculating the correlation coefficient ($r^2$). The detection limit and the quantitation limit were determined using 3.3×slope/δ, 10×slope/δ, and the respective equation.

TABLE 1

| HPLC conditions | |
|---|---|
| Column flow rate injection rate (volume) column temperature autosampler temperature | Luna C18 RP column (2.0 × 150 mm, 5 μm) 0.3 mL/min 5 μL 40° C. 4° C. |
| | min   A (%)   B (%) |
| Mobile phase | 0 1 6.5 8   90 90 10 10 90   10 10 90 90 10<br>8.5 15   90   10 |
| | A: 1.0% acetic-acid-containing aqueous solution<br>B: 1.0% acetic-acid-containing acetonitrile solution |
| Mass conditions: Ion source Curtain Gas Collision Gas Ion spray Voltage Source temperature Gas 1 Gas 2 | Turbo spray (Negative) 30 psi $N_2$ (Medium)- 4.0 kV 400° C. 40 psi 50 psi |

TABLE 2

| Component | DP (V) | EP (V) | CXP (V) | CE (eV) | Precursor m/z[M − H]⁻ | Product ion m/z[M − H]⁻ |
|---|---|---|---|---|---|---|
| Glycyrrhizin | −105 | −9.5 | −60 | −30 | 821.4 | 351.0 |
| Liquiritin | −40 | −10 | −24 | −28 | 417.1 | 255.0 |
| Liquiritigenin | −40 | −4 | −12 | −30 | 255.0 | 119.0 |
| Digoxin (IS) | −105 | −9.5 | −52 | −44 | 779.4 | 649.4 |

(3) Analysis Results

Quantitative analysis was performed on glycyrrhizin, liquiritin and liquiritigenin, the three main components of the licorice extract, using LC-MS/MS. As analysis results, glycyrrhizin, liquiritin, liquiritigenin and digoxin, the internal standard material, were confirmed to have molecular ions in the form of [M-H]⁻ at m/z 821.4, m/z 417.1, m/z 255.0 and m/z 779.4, respectively. When the collision energy of each compound was given as shown in Table 1, glycyrrhizin, liquiritin, liquiritigenin and digoxin, the internal standard material, were observed to produce ions at m/z 351.0, m/z 255.0, m/z 119.0 and m/z 649.4. Glycyrrhizin was detected at m/z 351.2 in the form of aglycon [M-H-2Glu]$^-$, in which two molecules of glucose were separated from m/z 821.4, liquiritin was detected at m/z 255.0 in the form of aglycon [M-H-Glu]$^-$, in which one molecule of glucose was separated from m/z 417.1, and liquiritigenin was detected at m/z 119.0 in the form of [M-H-C$_8$H$_6$O$_7$]$^-$, in which C$_8$H$_8$O$_8$ and H$_2$O molecules were separated from m/z 255.0.

In the established LC-MS/MS MRM mode of the licorice extract, glycyrrhizin, liquiritin, liquiritigenin and digoxin, the internal standard material, were detected at 7.14, 5.37, 6.22 and 6.44 min, respectively.

(4) Test for Drying of Licorice Extract

The powder was considered to be easy to store and use for application to a functional health food or medicinal food, and the extract solution obtained through extraction with 70% ethanol was subjected to a drying process such as spray drying, freeze drying, excipient addition, etc. As a result, there was no significant difference in contents of GA and LQ under spray-drying and freeze-drying conditions. Generally, it is known that freeze drying takes a longer time than spray drying and is expensive. Therefore, the spray-drying process was adopted for cost reduction by shortening the production time of the licorice extract and lowering preparation costs, and it is expected to be efficient to add dextrin (excipient) in order to ensure the stability of the raw material.

3. Comparison of Components of Each Extract

The components of Licorice extract 1 to Licorice extract 3 were measured. The results are shown in Table 3 below.

TABLE 3

| Licorice extract | GA (mg/g) | LQ (mg/g) | GA:LQ ratio | Remark |
|---|---|---|---|---|
| 1 (EX1) | 12.4 | 20.6 | 1.0:1.66 | Water extraction, paste |
| 2 (EX2) | 16.5 | 16.5 | 1.0:1.0 | 70% ethanol extraction, paste |
| 3 (EX3) | 20.6 | 12.4 | 1.66:1.0 | 70% ethanol extraction, powder |

GA: glycyrrhizin,
LQ: liquiritin

TEST EXAMPLES

1. Evaluation of Hepatotoxicity Reduction Efficacy in Cultured Hepatocytes In Vitro (1) Preliminary Evaluation of Cytotoxicity of Licorice Extract Hepatotoxicity was induced using acetaminophen in cultured hepatocytes (HepG2) as follows.

Specifically, a cytotoxicity test (MTT assay) was performed on the licorice extract. Cell viability was measured using HepG2 (hepatocellular carcinoma cell line) to evaluate cytotoxicity. On the day before the test, cells were aliquoted into a 96-well plate in an amount of 1×10$^4$ cells/well, and on the next day, the samples were treated at respective concentrations. After 24 hr, using a kit CCK-8 (cell counting kit-8; DOJINDO, Tokyo, Japan), 1/10 volume of the medium was added into each well in accordance with the method described in the manual, followed by incubation in a 5% CO$_2$ incubator at 37° C. for 2 hr and measurement of the activity of CCK-8 at a wavelength of 450 nm using a microplate reader.

As shown in FIG. 1A, based on the results of evaluation of whether the licorice extract (EX3) was toxic in cultured hepatocytes (HepG2), the licorice extract (EX3) did not show cytotoxicity up to 1.0%.

Thereafter, whether the licorice extract was able to reduce or inhibit hepatotoxicity induced by acetaminophen (APAP) was evaluated. In order to evaluate the extent of hepatotoxicity of APAP, HepG2 cells were treated with APAP at concentrations of 10 mM and 20 mM, respectively. Thereafter, the cells were treated with 0.1% and 1% of the licorice extract that did not show toxicity (EX3), and cell viability was measured through a cytotoxicity test.

As shown in FIG. 1B, the licorice extract (EX3) was confirmed to reduce hepatotoxicity induced by acetaminophen.

(2) Evaluation of Anti-Inflammatory Effect of Single Component Derived from Licorice Extract In order to evaluate the anti-inflammatory effects of single components derived from the licorice extract, BV2 cells were treated with glycyrrhizin, liquiritin and liquiritigenin at concentrations of 10, 20 and 50 μM, after which the inhibition of NO production by LPS (Lipopolysaccharide) was measured after 24 hr.

As shown in FIG. 2, all three components exhibited the inhibitory effect on the NO production with an increase in the concentration thereof, and in particular, all three components exhibited significant inhibition effect at 50 μM. Among the three components, liquiritigenin exhibited the greatest efficacy.

(3) Measurement of Effect of Single Component Derived from Licorice Extract on Molecular Biomarker In order to investigate the molecular biological mechanism of the anti-inflammatory effect of the single components derived from the licorice extract, the following test was conducted. BV2 cells were treated with an inflammation inducer LPS, after which the extent of inhibition of the increase in proinflammatory cytokines, iNOS (inducible nitric oxide), COX2 (cyclooxygenase-2), etc. by three components (glycyrrhizin, liquiritin and liquiritigenin) was measured based on changes in mRNA using a PCR technique.

As shown in FIGS. 3A, 3B and 3C, all of the licorice-derived single components showed the inhibitory effects of NO production (anti-inflammatory), and liquiritin (3B) decreased the expression of iNOS and COX2 more strongly than glycyrrhizin (3A), and liquiritigenin (3C) also exhibited reduction effects.

Also, as shown in FIGS. 4A, 4B and 4C, the expression of inflammation-related cytokines (TNF-α, IL-1β, IL-6) was inhibited more strongly by glycyrrhizin (4A) than by the other two components.

(4) Evaluation of Hepatotoxicity Reduction Efficacy of Single Component Derived from Licorice Extract Hepatotoxicity was induced in cultured hepatocytes (HepG2) using t-butyl hydroperoxide (t-BHP) in accordance with the method disclosed in the literature (Lee et al., Liver International, 2005; 25:1069-1073). As shown in FIGS. 5A and 5B, t-BHP exhibited dose-dependent hepatotoxicity 3 hr and 24 hr after treatment.

Glycyrrhizin, liquiritin and liquiritigenin were used for cell treatment at a concentration of 100 μM, and it was confirmed that they did not induce toxicity in the cells. The cell viability for each component was measured to be 95% or more, which means that there was no cytotoxicity. On the other hand, upon treatment with t-BHP, cell viability was drastically lowered to about 30% (FIG. 6).

As shown in FIG. 6, in cultured hepatocytes, glycyrrhizin, liquiritin and liquiritigenin exhibited hepatotoxicity inhibition effects increased with the treatment concentration thereof.

2. Evaluation of Hepatoprotective Efficacy of Licorice Extract In Vivo (1) Evaluation of Effect of Licorice Extract on Hepatotoxicity Marker ICR mice were intraperitoneally administered with 1.5 mmol/kg of t-BHP to thus induce hepatotoxicity. 3 days before t-BHP treatment, the licorice extract (EX3, 300 mg/kg) was administered orally for 3 days. When the mice were treated with t-BHP, AST (aspartate aminotransferase or GOT: glutamic oxaloacetic transaminase) and ALT (alanine aminotransferase or GPT: glutamic pyruvate transaminase) in the blood were increased, and thus hepatotoxicity was confirmed to be induced.

As shown in FIGS. 7A and 7B, when the mice were pretreated with the licorice extract (EX3), the increase in AST and ALT in the blood was significantly lowered and thus hepatotoxicity was confirmed to decrease. As for the hepatoprotective effect, GOT/GPT reduction efficacy of the licorice extract (EX3), was observed to be similar or superior to that of milk thistle extract, which is known to have hepatoprotective efficacy.

(2) Evaluation of Effect of Licorice Extract on Expression of Proinflammatory Cytokines In order to measure the effect of the licorice extract on molecular biomarkers related to the hepatoprotective efficacy in mice, the following test was conducted. ICR mice were intraperitoneally administered with 1.5 mmol/kg of t-BHP to thus induce hepatotoxicity. 3 days before t-BHP treatment, the licorice extract (EX3, 300 mg/kg) was administered orally for 3 days.

As shown in FIGS. 8A, 8B, 8C and 8D, when the mice were treated with t-BHP, the expression of proinflammatory cytokines such as TNF-α, IL-1β and IL-6 was increased in the liver tissue, and oral administration of the licorice extract (EX3) for 3 days was effective at inhibiting the increase in the expression of TNF-α, IL-1β and IL-6.

3. Evaluation of Hepatoprotective Effect of Licorice Extract in Animal Model with Alcoholic Liver Injury (1) Animal Test Method An alcohol-containing diet was administered to small animals (mice or rats) to induce alcoholic liver injury, after which the following test was conducted to determine the hepatoprotective effect of the licorice extract (EX3).

Mice (C57BL/6N, 6-week-old, male) were divided into ① normal diet group (control), ② alcohol diet group, ③ alcohol diet+licorice extract (EX3) treatment group, and ④ alcohol diet+milk thistle extract treatment group (10 mice/group), and the ethanol-containing diet (Ethanol Lieber-DeCarli liquid diet) was fed to the corresponding groups for 4 weeks in a pair-feeding manner to thus induce alcoholic liver injury. The composition and the feeding period of the normal diet and the alcohol-containing diet are shown in Table 4 below. The feed was purchased from Dyets, USA, and was dissolved in an amount of 221.78 g in 1 L of water for the normal diet group. The alcohol-containing diet was prepared by mixing 132.18 g of feed and 67.3 ml of 95% alcohol and adding water thereto so as to reach a final volume of 1 L.

TABLE 4

| Component | Amount |
|---|---|
| Normal diet (1000 kcal/L) | |
| Fat | 35% |
| Protein | 18% |
| Carbohydrate | 47% |
| Alcohol-containing diet (1000 kcal/L) | |
| Fat | 35% |
| Protein | 18% |
| Carbohydrate | 11% |
| Ethanol | 36% |

The respective corresponding groups were orally administered with the licorice extract (EX3) (100 mg/kg) and the milk thistle extract (100 mg/kg) daily for the same period as the alcohol diet feeding period. After 4 weeks, the blood and organs (liver, kidney, etc.) of each group were collected.

(2) Method of Analyzing Serum Biochemical Markers

Sera were collected from blood samples by centrifugation (3,500 g, 10 min, 4° C.). ALT (alanine aminotransferase), AST (aspartate aminotransferase), and gamma-GTP (gamma-glutamyl transpeptidase) in the sera were determined using an automated blood analyzer (Abbott Laboratories, Abbott Park, Ill.).

The mouse liver was homogenized, followed by extraction with chloroform/methanol+sodium chloride solution, after which the triglyceride content in the liver was determined.

For the analysis of accumulated fat in liver tissues, the left outer lobe of the liver was cut into sections, and the tissue sections were fixed with 10% buffered neutral formalin for 6 hr and then cut to a thickness of 4 mm, followed by H&E staining before observation. The liver tissue frozen for staining (Oil Red O) was cut to a thickness of 10 mm, attached to a microscope slide, and dried at room temperature for 24 hr. The liver tissue sections were stained with a dye (Oil Red O, Sigma, St. Louis, Mo.) reagent for 10 min, washed with water and then observed using an optical microscope.

In order to determine the glutathione content in the liver, the mouse liver was homogenized, added with 20-fold volume of ice-cold methanol, pulverized with a pulverizer (Polytron) and then centrifuged. The supernatant was used for analysis. Then, derivatization using OPA (O-phthaldialdehyde) was performed. HPLC equipped with a reverse phase column (column, Kromasil) and a detector (FS-920 fluorescence detector, JASCO, JAPAN) were used for determination. In order to use mobile phase gradient, two pumps (pump, Jasco Model PU-980, Jasco Co., Tokyo, Japan) were used.

(3) Results of Evaluating Changes in Liver Injury Marker in Blood

Biochemical markers of liver injury were determined as above and the results are shown in FIGS. 9A, 9B and 9C. As shown in FIGS. 9A, 9B and 9C in the chronic (4-week administration) alcohol diet group (Alcohol), the levels of ALT, AST, and GTP, which are liver injury markers, were increased compared to the normal diet group (control), from which liver injury was confirmed to be induced by the chronic alcohol diet. In the group administered with licorice extract, the levels of ALT, AST and GTP, which were increased due to liver injury induced by the chronic alcohol diet, were significantly reduced, and the extent of reduction thereof was superior or similar to that of the milk thistle extract, which is known to have liver function improvement efficacy.

(4) Results Pertaining to Triglyceride Content and Fat Accumulation in Liver Tissue The triglyceride content in the liver tissue was measured as described above. The results are shown in FIG. 10A, and the fat accumulation results are shown in FIG. 10B.

The initial symptoms of chronic alcohol ingestion are fat accumulation in the liver tissue, which can lead to fatty liver disease due to persistent alcohol ingestion. As shown in FIG. 10A, based on the results of determining the triglyceride content in the mouse liver, the triglyceride content in the liver of the alcohol diet group was drastically increased compared to that of the normal diet group.

In the group administered with licorice extract, the fat accumulation due to alcohol consumption was significantly reduced, and the extent of reduction thereof was remarkably superior to that of the group administered with milk thistle extract. These results were also apparent from the results of histological staining (oil red staining) (FIG. 10B) and showed a tendency of greater efficacy than the milk thistle extract group (the positive control group). Therefore, the licorice extract was confirmed to shut out fat accumulation due to alcohol ingestion in liver tissue significantly, thus exhibiting hepatoprotective efficacy.

(5) Results of Determining of Glutathione (GSH) Content in Liver Tissue

Glutathione is a typical endogenous antioxidant synthesized in the body. Reduction of glutathione due to chronic alcohol ingestion is strongly correlated with tissue damage.

As shown in FIG. 11, in the chronic alcohol diet group, GSH levels in liver tissues were significantly reduced compared to the normal diet group. In the group administered with licorice extract, GSH content was maintained at a level similar to that of the normal diet group. Particularly, in the group administered with milk thistle extract, an effect of inhibiting reduction in GSH content was observed, but the extent thereof was not similar to that of the normal diet group. In contrast, in the group administered with licorice extract, it was confirmed that GSH content was maintained at a level similar to that of the normal diet group and thus the effect of the licorice extract on maintaining the endogenous antioxidant was remarkably superior to that of the known substance to have hepatoprotective efficacy (positive control group). This suggests that the protecting mechanism of the licorice extract against alcoholic liver injury is partially related to the maintenance of the antioxidant system in liver tissue.

4. Evaluation of Liver Function Protection Efficacy Depending on Ratio of Active Component Composition in Licorice Extract (1) Animal Test ICR mice were treated with t-BHP (1.8 mmol/kg) to thus induce hepatotoxicity, and 3 days before treatment with t-BHP, three licorice extract (S-1: Licorice extract 1, S-2: Licorice extract 2, S-3: Licorice extract 3) were orally administered at a dose of 300 mg/kg. 24 hr after induction of hepatotoxicity, blood samples of the ICR mice were collected and GOT (AST) and GPT (ALT) were determined. The liver tissue was homogenized, and protein and mRNA were obtained. Then, it was evaluated whether or not proinflammatory cytokines were expressed.

(2) Results of Analysis of Liver Function Protection Marker

The results of determining GOT (AST) and GPT (ALT) in the blood of hepatotoxicity-induced mice are shown in FIGS. 12A and 12B. As shown in FIGS. 12A and 12B, when the mice were treated with t-BHP, GOT (AST) and GPT (ALT) in the blood were increased and thus hepatotoxicity was confirmed to be induced. In the groups administered with Licorice extract 1 (S-1), Licorice extract 2 (S-2), and Licorice extract 3(S-3), the levels of GOT (AST) and GPT (ALT) were remarkably decreased. In particular, the extent of decrease in the Licorice extract 3 (S-3) group was greater than those in the other licorice extract groups.

(3) Results of Determining of Proinflammatory Cytokines

The results of evaluation of whether or not proinflammatory cytokines were expressed from liver tissue protein and mRNA of hepatotoxicity-induced mice are shown in FIG. 13. As shown in FIG. 13, when the mice were treated with t-BHP, the expression of proinflammatory cytokines, such as TNF-α, IL-1β, and IL-6, was increased in the liver tissue. In the groups administered with Licorice extract 1 (S-1), Licorice extract 2 (S-2), and Licorice extract 3(S-3), the expression of proinflammatory cytokines was inhibited. In particular, the extent of inhibiting the expression in Licorice extract 3 (S-3) group was greater than those in the other licorice extract groups.

Therefore, the licorice extract comprising GA and LQ at a ratio of 1.66:1.0 (Licorice extract 3) can be concluded to exhibit superior hepatoprotective efficacy compared to the other licorice extracts having different component ratios.

We claim:

1. A method for treating an alcoholic fatty liver disease comprising: administering to a subject having an alcoholic fatty liver disease a pharmaceutical composition comprising an effective amount of a licorice extract and a pharmaceutically acceptable diluent or carrier, and thereby treating the alcoholic fatty liver disease,
    wherein the licorice extract comprises as effective ingredients glycyrrhizin and liquiritin at a weight ratio of 1.66:1.

* * * * *